United States Patent [19]

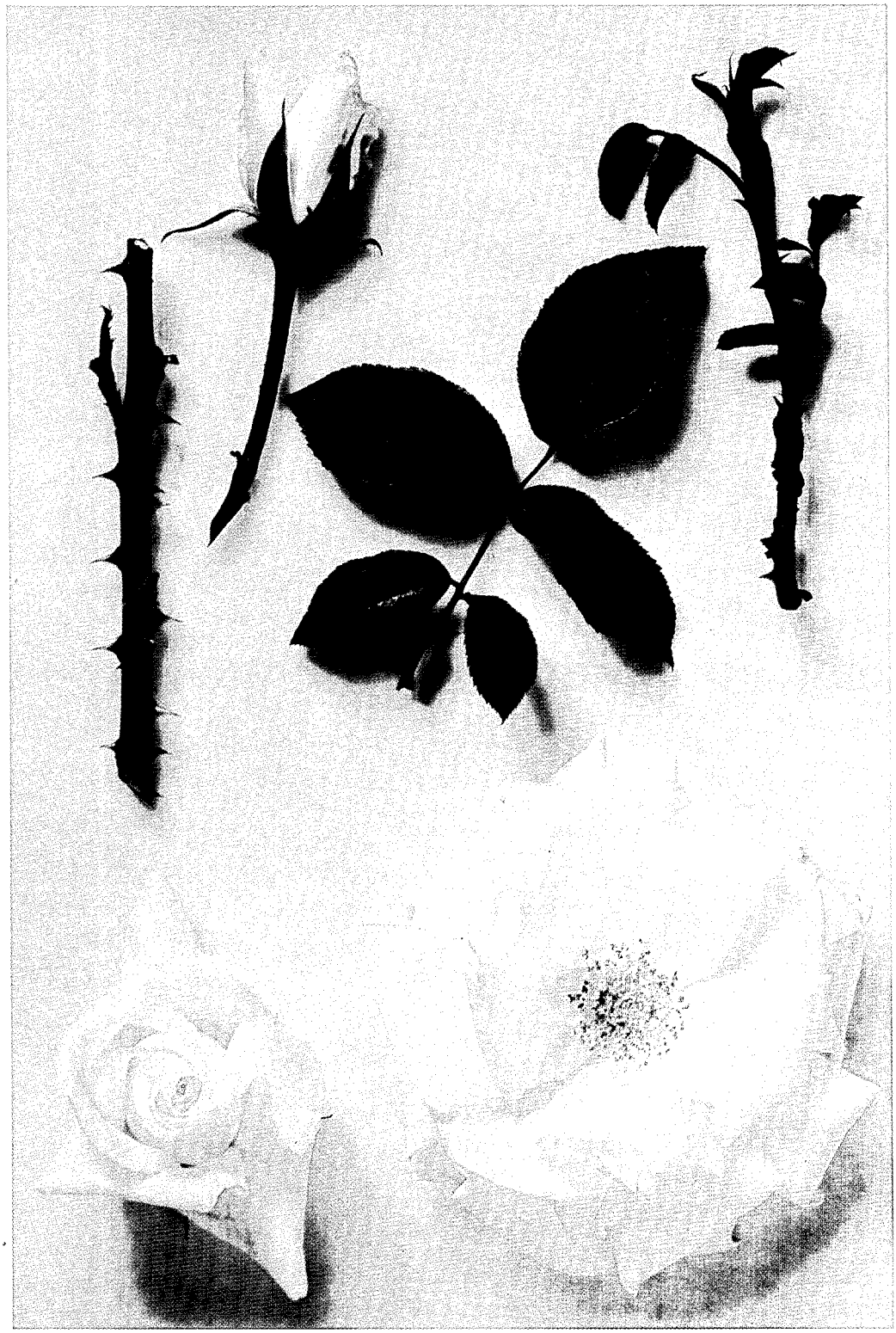

Warriner

[11] Plant 4,167

[45] Dec. 20, 1977

[54] ROSE PLANT

[75] Inventor: William A. Warriner, Tustin, Calif.

[73] Assignee: Jackson & Perkins Co., Medford, Oreg.

[21] Appl. No.: 745,459

[22] Filed: Nov. 26, 1976

[51] Int. Cl.[2] ..... A01H 5/00

[52] U.S. Cl. ..... Plt./14

[58] Field of Search ..... Plt./14

*Primary Examiner*—Robert E. Bagwill

*Attorney, Agent, or Firm*—Klarquist, Sparkman, Campbell, Leigh, Hall & Whinston

[57] ABSTRACT

A novel hybrid tea rose cultivar characterized by a vigorous, upright growth habit, white blossoms, and resistance to powdery mildew.

1 Drawing Figure

The present invention relates to a new and distinct cultivar of rose plant of the hybrid tea class which was originated by me by crossing two unnamed cultivars of roses.

The primary objective of this breeding was to produce a hybrid tea cultivar of vigorous, upright growth with the possibility that the color would be white, coral, pink or yellow and the flowers large and plentiful. The objective was fully achieved in this white flowered cultivar, as evidenced by the following unique combination of characteristics which are outstanding in this new cultivar and which distinguish it from its parents as well as from all other cultivars of which I am aware:

1. A vigorous, upright habit of growth.
2. Garnette Brown new foliage developing into dark green mature foliage, quite resistant to rose powdery mildew.
3. Buds of a very light tint of Egyptian Buff (W) with the tip edged Carmine (W).
4. Partly open to open flowers white with 18 to 25 petals.
5. Large prickles slightly hooked downward.
6. Very slight fragrance.

Asexual reproduction of this new cultivar by budding as performed at Wasco, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color terminology in accordance with *Wilson's Horticultural Color Chart,* except where ordinary dictionary significance of color is indicated.

Parentage: Seedling.

*Seed parent.*—Unnamed variety.

*Pollen parent.*—Unnamed variety.

Classification:

*Botanical.*—Rosa hybrid.

*Commercial.*—Hybrid Tea.

FLOWER

Observations made from specimens grown at Irvine, Calif., in October, 1976.

Blooming habit: Continuous.

Bud:

*Size.*—1 to 1¼ inches when petals start to unfurl.

*Form.*—Long, pointed.

*Color.*—When sepals first divide Near Egyptian Buff (407/3) changing to white when petals unfold; petal tips usually tinted with Carmine (21/1) fading to white as petals unfold; when half blown; upper side of petals nearly white, except some tinting of Egyptian Buff (407/3) in unopened petals; lower side of petals nearly white, except some tinting of Egyptian Buff (407/3) in unopened petals.

*Sepals.*—Color: Outer surface Scheeles Green (860) overlaid along midrib and other irregular areas with Garnett Brown (00918/3); inner surface Scheeles Green (860/3) with much white tomentum; three appendaged sepals lightly appendaged; two unappendaged sepals hairy edged.

*Receptacle.*—Color: Near Scheeles Green (806); size — large; surface — smooth.

*Peduncle.*—Length: long; surface: prickly and glandular; color: light green; strength: stiff, erect.

*Opening.*—Petals curl and unfold in spiral fashion.

Bloom:

*Size.*—Large. Average open size 5".

*Stems.*—Long, strong.

*Borne.*—Singly and several together.

*Form.*—When first open: flat. Permanence: retains its form to the end.

*Petalage.*—Number of petals under normal conditions: 18 to 25.

*Color.*—Center of open flower: upper side of petals — white; reverse side of petals — white; base of petals — small area near Empire yellow (603) at point of attachment; general tonality from a distance — white.

*Variegations.*—Only as noted.

*Discoloration.*—General tonality at end of first day: white; general tonality at end of third day: white.

*Fragrance.*—Slight.

Petals:

*Texture.*—Thick.

*Shape.*—Round.

*Form.*—Edges slightly quilled.

*Arrangement(petal).*—Loosely imbricated.

*Persistence.*—Drop off cleanly.

*Lastingness.*—On the plant: long; as cut flower: long.

Reproductive parts:

*Stamens, anthers.*—Medium; color: yellow. Arrangement: regular around styles.

*Filaments.*—Primrose yellow (601).

*Pollen.*—Gold yellow.

*Styles.*—Color: lower half light green, upper half reddish.

*Stigmas.*—Color: yellow.

PLANT

Form: Bush.

Growth: Vigorous, upright, branching.

Foliage: Number of leaflets on normal mid-stem leaves, 5.

*Size.*—Large.

*Quantity.*—Normal.

*Color.*—New foliage: near Garnette Brown (00918); old foliage: between Spinach Green (0960) and Ivy Green (0001060/3).

*Shape.*—Oval pointed.

*Texture.*—Semi-glossy.

*Edge.*—Serrated.

*Serration.*—Single, small.

*Petiole.*—Rachis: Color — green; underside — prickles.

*Stipules.*—Long, bearded.

*Disease resistance.*—Normally resistent to mildew, under normal growing conditions at Irvine, Calif.

Wood:

*New wood.*—Color: dark green. Bark: smooth.

*Old wood.*—Color: green. Bark: smooth.

Prickles:

*Quantity.*—On main stalks from base: many; on laterals from stalk: many.

*Form.*—Broad base, hooked downward very slightly.

*Color when young.*—Brown.

*Position.*—Irregular.

Small prickles: None.

I claim:

1. A new and distinct cultivar of rose plant of the hybrid tea class, substantially as herein shown and described, characterized particularly as to novelty by the unique combination of a vigorous upright habit of growth, Garnette Brown new foliage maturing to dark green, nearly white buds with a tint of Egyptian Buff and tipped with Carmine, opening to white blooms of 18 to 25 petals, large prickles angled slightly downward and a light fragrance.

* * * * *

UNITED STATES PATENT AND TRADEMARK OFFICE

CERTIFICATE OF CORRECTION

PATENT NO. : PP 4167

DATED : December 20, 1977

INVENTOR(S) : William A. Warriner

It is certified that error appears in the above-identified patent and that said Letters Patent are hereby corrected as shown below:

Column 2, line 19 - "806" should be --860--.

Signed and Sealed this

*Eighteenth* Day of *April 1978*

[SEAL]

*Attest:*

RUTH C. MASON
*Attesting Officer*

LUTRELLE F. PARKER
*Acting Commissioner of Patents and Trademarks*